United States Patent [19]

Hejndorf

[11] Patent Number: Plant 7,597

[45] Date of Patent: Jul. 23, 1991

[54] MINIATURE ROSE PLANT RUISKOLPI

[75] Inventor: Poul Hejndorf, Brabrand, Denmark

[73] Assignee: DeRuiter's Nieuwe Rozen B.V., Netherlands

[21] Appl. No.: 497,482

[22] Filed: Mar. 22, 1990

[51] Int. Cl.[5] ..... A01H 5/00

[52] U.S. Cl. ..... Plt./9

[58] Field of Search ..... Plt./9

*Primary Examiner*—James R. Feyrer

*Attorney, Agent, or Firm*—Christie, Parker & Hale

[57] ABSTRACT

A new variety of miniature rose having attractive deep pink flowers produced on a good pot forcing plant.

2 Drawing Sheets

SUMMARY OF THE INVENTION

The present invention relates to a new and distinct variety of rose plants of the miniature rose class, which was discovered by me as a mutation in a controlled planting of the rose known as "Ruimissa". The varietal denomination of this new rose is "Ruiskolpi".

Among the novel characteristics possessed by this new variety which distinguishes it from its parent and all other varieties of which I am aware are its attractive deep pink flowers borne on a plant particularly suited for production of flowering pot plants and that can also be reproduced through propagation by cuttings and grafting.

Flowers of the new variety are long lasting on the plant. "Ruiskolpi" differs from its parent variety "Ruimissa" in flower coloring. Flowers of the new variety are softer pink and show different color variations between outer and inner petals as compared to "Ruimissa".

Asexual reproduction by grafting and cuttings, of the new variety as performed in Sabro, Denmark, shows that the foregoing and other distinguishing characteristics come true to form and are established and transmitted through succeeding propagation.

The accompanying drawings show typical specimens of the vegetative growth and flowers of the new variety in different stages of development and depicted in color as nearly true as it is reasonably possible to make the same in color illustration of this character.

BRIEF DESCRIPTION OF THE DRAWINGS

One of the photo illustrations shows details of the new miniature rose variety in substantially true flower color and the other illustration shows the plant growth and blooming habits but with somewhat variant flower coloring.

DESCRIPTION OF THE PREFERRED EMBODIMENT

The following is a detailed description of my new variety, with color terminology in accordance with The Royal Horticultural Society Color Chart (R.H.S.C.C.) and horticultural terminology in accordance with standard terminology used in UPOV-approved horticultural guidelines. The terminology used in color description herein refers to plate numbers in the aforementioned color chart.

Parentage: Mutation of "Ruimissa".
Class: Miniature.

In the illustration showing details of the new variety "Ruiskolpi", there is seen the top of a young shoot, 1; compound three, five and seven leaflet leaves, 2, 3, and 4, respectively; a stem, 5; a flower bud, 6 showing color; a flower bud, 7, after sepals separate; a flower 8 about one-third to one-half open; and a flower, 9, fully open. Also shown are flower stems, 10, 11, and 12, with reproductive organs.

The other illustration depicts the plant growth habit and blooming habit of the new variety.

The following further horticultural observations were made of specimens grown under glass in Holland.

FLOWER

Blooming habit: Nearly continuous, very floriferous, early flowering.

A. Bud:
- (1) *Size.*—Medium.
- (2) *Form.*—Ovate (before separation of sepals).
- (3) *Color.*—As sepals divide, bud color is near 47D.
- (4) *Sepals.*—Longer than bud, simple to foliated.
- (5) *Peduncle.*—Length — about 4 to 5 cm. Aspect — straight; Strength — erect; Color — medium green.

B. Bloom:
- (1) *Flowers.*—Average size for miniature; Viewed from top — round; Viewed from side, (A) Upper part of fully opened flower — flat to flattened convex, (B) Lower part of fully opened flower — flattened convex.
- (2) *Size.*—Average size when fully expanded — about 5 to 6 cm.
- (3) *Borne.*—Singly, to a stem and small clusters.
- (4) *Form.*—Ovoid to pointed at first, opening to good form and then becoming flat; out petals reflex to points; inner petals roll under slightly.
- (5) *Petalage.*—Number of petals under normal conditions — about 24 to 30, fully double.
- (6) *Color.*—As can be seen in the detail photo illustration, after sepals separate coloring of bud is near 47D to 51B; when sepals part and petals begin to unfurl, predominant color is near 47C and 47D; viewing petals' top surface in the open bloom, flower color ranges from near 51C at outer petals to near 48A at flower center where petals bunch; some petal apices and margins occasionally show darker hues, near 50B; petal top and reverse are of similar coloring; coloring at point of petal attachment is near 4D. Overall tonality from a distance is an attractive, relatively pure, deep pink.

C. Petals:
(1) *Texture.*—Medium to thick.
(2) *Appearance.*—Inside velvety and outside satiny.
(3) *Form.*—Broad obovate; Undulation at margin — weak.
(4) *Arrangement.* 13 Regularly arranged, imbricated.
(5) *Petaloids in center.*—Few.
(6) *Persistence.*—Drop off cleanly.
(7) *Fragrance.*—Slight to none.
(8) *Lasting quality.*—Very long lasting quality on plant.

REPRODUCTIVE ORGANS

A. Stamens, filaments and anthers:
*Arrangement and color.*—Regularly arranged around styles; Color — filaments yellow.
B. Pollen:
*Color.*—Yellow.
C. Styles: Even medium length, stigma well above mouth of receptacle, yellow-green, upper half little to no hair, bunched.
D. Stigma: Full, extends to same level as anthers.
E. Hips: Medium for miniature, pitcher-shaped.

PLANT

A. Form: Upright to bushy.
B. Growth: Vigorous.
Height attained.—About 20 to 30 cm.
C. Foliage: Compound 3, 5 and 7 leaflets.

(1) *Size.*—Medium for miniature.
(2) *Quality.*—Abundant.
(3) *Color.*—Foliage at time of first flowering — medium to dark green.
(4) *Shape.*—Oval, pointed.
(5) *Texture.*—Upper side is weakly glossy; under side is matte.
(6) *Edge.*—Serrate.
(7) *Serration.*—Ordinary, acuminate apices.
(8) *Leaf stem.*—Color — medium green.
(9) *Stipules.*—Medium length, slightly bearded, medium to light green, distinct auricle.
(10) *Leaflet.*—Cross section — flat; Terminal leaflet — very short; narrow; obtuse base; Petiole — short; litte or no undulation at margin.
(11) *Pedicel.*—Few hairs or prickles.

D. Wood:
(1) *New wood.*—Color — medium green with purplish margin; Young shoot — weak anthocyanin coloration.
(2) *Old wood.*—Color — medium green.

E. Prickles: Very few.
*Color.*—Light pink to tan.
*Position.*—Irregular.

F. Winter hardiness.—Needs protection outdoor in severe climates.

I claim:

1. A new and distinct variety or rose plant of the miniature rose class, substantially as shown and described, characterized particularly by attractive deep pink flowers, which are long lasting on the plant, borne on a plant suitable for growing in pots.

* * * * *

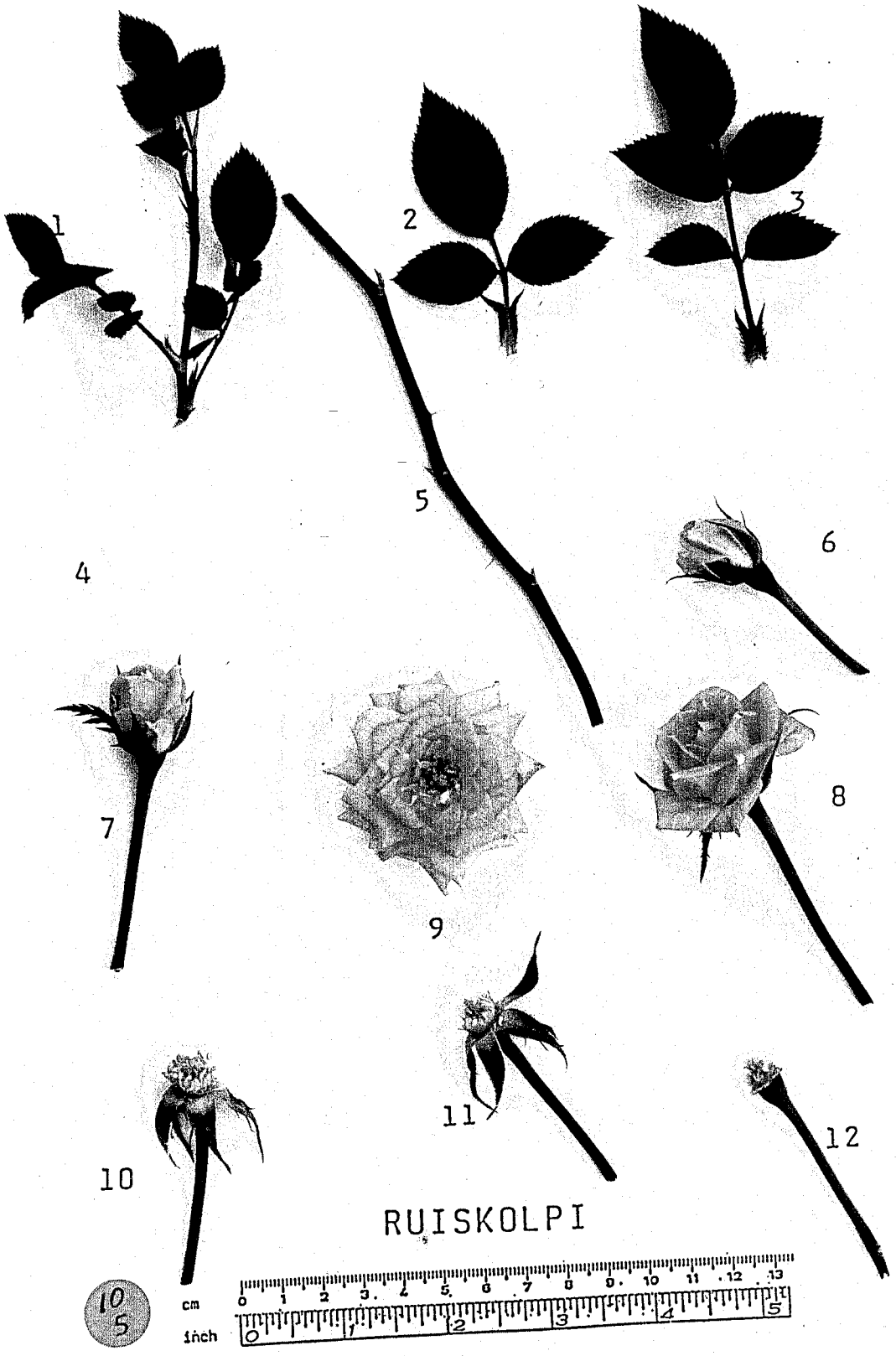
1
2
3
4
5
6
7
8
9
10
11
12
RUISKOLPI
cm
inch

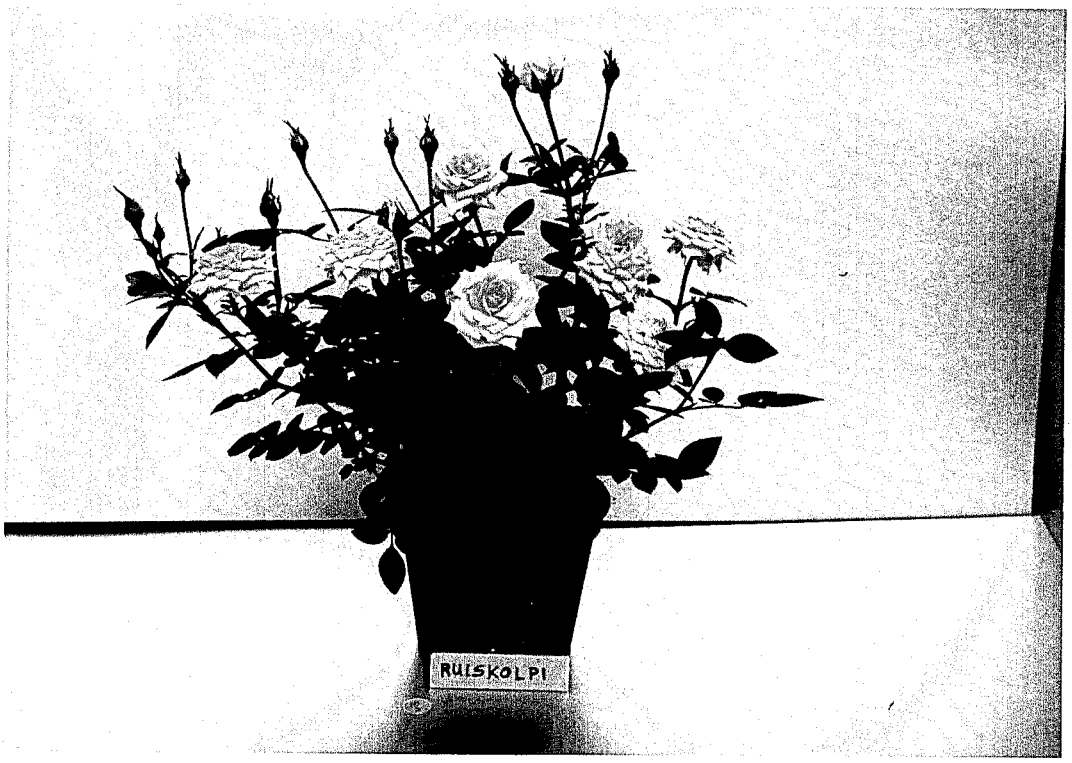
RUISKOLPI